United States Patent [19]

Brown et al.

[11] 4,028,444

[45] June 7, 1977

[54] HUMIDIFIER AND AUTOMATIC CONTROL SYSTEM THEREFOR

[75] Inventors: Allen C. Brown, Acton; Neil R. Hattes, Danvers; Theodore B. Eyrick, Andover, all of Mass.

[73] Assignee: Chemetron Corporation, Chicago, Ill.

[22] Filed: Mar. 25, 1974

[21] Appl. No.: 454,503

[52] U.S. Cl. .................. 261/122; 261/142; 261/DIG. 65; 55/274; 55/227; 128/193; 219/275; 137/558
[51] Int. Cl.² ............................. B01D 47/02
[58] Field of Search ............ 261/DIG. 65, 64, 65, 261/142, 122; 55/244, 274, 245, 248, 164, 227, 257; 128/194, 193, 186, 196, DIG. 2; 219/271, 272, 273, 275, 362; 137/558

[56] References Cited

UNITED STATES PATENTS

| | | | |
|---|---|---|---|
| 3,593,712 | 7/1971 | Weaver et al. | 128/194 |
| 3,610,880 | 10/1971 | Kreiberg | 219/273 |
| 3,735,568 | 5/1973 | Beck | 261/142 |
| 3,757,082 | 9/1973 | Goicoechea | 261/DIG. 65 |
| 3,793,810 | 2/1974 | McPhee | 128/194 |
| 3,882,887 | 5/1975 | Rekai | 137/558 |

*Primary Examiner*—Bernard Nozick
*Attorney, Agent, or Firm*—Jones, Tullar & Cooper

[57] ABSTRACT

A humidifier system for delivering breathing gases such as air or oxygen from a respirator, anesthesia machine, oxygen source, or the like to a patient under controlled conditions of temperature and humidity is disclosed. The humidifier comprises a support housing adapted to receive a removable water tank, the housing also containing a low water sensing system, a water heating means, and a system for sensing and for regulating the temperature of the water in the tank. The tank includes an air inlet leading to a diffuser chamber, from which air flows through a diffuser plate, through the water in the humidifier, and thence to an outlet for delivery to the patient. The breathing gases are forced through the water tank under positive pressure and thereby are heated and humidified prior to delivery.

16 Claims, 10 Drawing Figures

HUMIDIFIER AND AUTOMATIC CONTROL SYSTEM THEREFOR

BACKGROUND OF THE INVENTION

The present invention relates, in general, to an improved apparatus for humidifying air and other gases, and more particularly to a humidifier system for breathing gases including means for directing the flow of gas through a water chamber, an alarm system for sensing the water level in the chamber, and means for sensing and controlling the temperature of the water, whereby warm, moist breathing gases may be supplied to a patient.

In the use of positive pressure respirators in the treatment of patients, it is frequently necessary to deliver breathing gas directly into the patient's trachea by an endotracheal tube or tracheostomy tube, thereby bypassing the patient's normal physiological humidifying and temperature regulating mechanisms. It is well known that when this is done, it is necessary to deliver a breathing gas that has been warmed and humidified in order to avoid not only patient discomfort but the very real problem of seriously injuring the lungs of the patient. To this end, numerous devices have been developed in the prior art to treat the air prior to delivery to the patient, but these have not been entirely satisfactory, since in general they do not provide adequate control of the delivered air. For example, many commercially available humidifiers fail to provide a sensor or an alarm system to indicate when the humidifier is low on water, do not provide accurate control of the temperature of the breathing gas, and do not provide any means for protecting the humidifier from contamination by condensate or other foreign matter that may return to the humidifer by way of the outlet.

One of the more common systems available in the prior art for supplying humidified gas to a patient involves the use of an atomizer or nebulizer that mechanically separates the water into tiny liquid droplets which are injected into and combine with the flow of delivered gas. Such a system, however, presents serious problems since it is very difficult to control the temperature of the humidified gas that is delivered to the patient. Further, the system does not provide means for compensating for changes in the flowrate of the breathing gas, and does not provide any means for automatically sensing and indicating the need for additional water, so that it is possible for the system to become inoperative as a humidifier without providing any warning to the operator. Finally, the system has no means for protecting the humidifier from contamination via the outlet.

Another common humidifier system causes the breathing gas to be directed through a volume of heated water prior to reaching the patient and thus avoids the problems inherent in the nebulizer approach, but has not been found satisfactory since it provides a relatively low level of moisture in the outlet gas. Furthermore, the system has no provision for automatically sensing and indicating when the unit is low on water, and provides no protection against contamination through the outlet.

An improved version of the foregoing approach has been developed in which a diffusing or bubbling plate containing numerous small holes is placed in the path of the air flow. The breathing gas is delivered into a volume of water below the bubble plate and passes upwardly through the plate. The air flow is broken into small bubbles to increase the surface area of gas exposed to the water located above the plate, prior to delivery of the gas to the patient. Although this method increases the amount of moisture in the air, such systems in the prior art have not been entirely satisfactory since it has been found to be difficult to control the temperature of the humidified gas delivered to the patient because the diffusing plate causes an air barrier to form which varies in thickness between breaths. Such prior art systems also have made no provision for automatically sensing and indicating sensing and indicating the need for additional water, and have provided no protection against the possibility of contaminants entering the humidifier through the breathing gas outlet.

Because such prior art systems provide inadequate control of the breathing gas temperature and moisture content, they have not been considered to be entirely reliable from the standpoint of patient safety and comfort, and accordingly have been unsatisfactory. In addition, the improvement of water and gas contact in the humidifier and improvement in the flow path to the patient in an attempt to provide greater stability and control in moisture content and gas temperature leads, in some cases, to an increased possibility of contamination of the water supply by bacteria from the patient. It has been found, for example, that when the warm moist air from the humidifier is delivered to the patient through a breathing tube, the air will cool and condensate will form on the inner surface. Condensate formed near the patient may pick up bacteria from the patient's respiratory tract, and any return flow of the condensate to the humidifier may carry such bacteria to the humidifier water supply, where it can proliferate and thus contaminate the supply.

Many of the attempts to meet these problems have resulted in complex, expensive humidifier systems which have been difficult to manufacture, hard to maintain in good working order, have required constant attention, and have thus generally been unsatisfactory.

SUMMARY OF THE INVENTION

It is, therefore, an object of the present invention to provide a breathing gas humidifier which is capable of producing both high levels of humidity and accurate breathing gas temperature control, yet is simple in construction and reliable in operation.

It is another object of the invention to provide a humidifier which provides a high degree of surface contact between the breathing gas and the water through which the gas passes, while producing a relatively constant humidity which is independent of the breathing gas flowrate, thereby insurance improved reliability and patient safety and comfort.

It is another object of the invention to provide a humidifer for a flowing gas wherein a high level of humidity is produced and wherein the temperature of the outflowing gas is accurately controlled and is independent of the volume of humidifying water between the level at which refilling is required and the refilled level.

Another object of the invention is to provide an optical sensing means for remotely determining the water level in order to indicate and warn of the need for adding water to the humidifier.

A further object of the invention is the provision of a disposable contaminant trap in the outlet path of the humidified gas to protect the humidifer water supply from contamination.

Briefly, the present invention is directed to a humidifier unit incorporating a temperature and water level control system. The humidifier includes an outer support housing and an inner liquid, or water, container through which the gas to be humidified is directed. The outer housing incorporates a base on which rests a heating element for the water container, the side walls for positioning the container over the heater. Means are provided to removably secure the container within the outer housing and in intimate engagement with the heater. A rear wall for the outer housing carries the control circuitry for the heater and for an optical level sensor and alarm.

The inner container includes side walls of transparent plastic, defining an open top and an open bottom. A thin metal plate closes the bottom of the container and forms a heat transfer medium for conveying heat to the liquid within the container from the heating element. The top of the container is closed by a cover which carries an inlet tube, through which air is introduced into the container, and an outlet opening adapted to receive a removable contaminant trap and outlet fitting.

Secured at the bottom of the inlet tube, and defining a diffuser chamber near the bottom of the container, is a horizontal diffuser plate through which gas from the inlet must pass in order to reach the outlet. The diffuser plate breaks the inlet gas stream into macroscopic bubbles which then pass upwardly through the water in the container and pass to the outlet. A light-reflecting prism is formed on one wall of the inner container and is positioned adjacent corresponding optical sensing means located in the rear wall of the outer housing when the container is positioned within the housing. The reflectivity of the prism is affected by the water level in the container, enabling the optical sensors to detect when the water supply in the container requires replenishment.

BRIEF DESCRIPTION OF THE DRAWINGS

The foregoing and additional objects, features, and advantages of the present invention will become evident from a consideration of the following description of a preferred embodiment of the invention, taken in conjunction with the accompanying drawings, in which.

DESCRIPTION OF A PREFERRED EMBODIMENT

Figure 1:
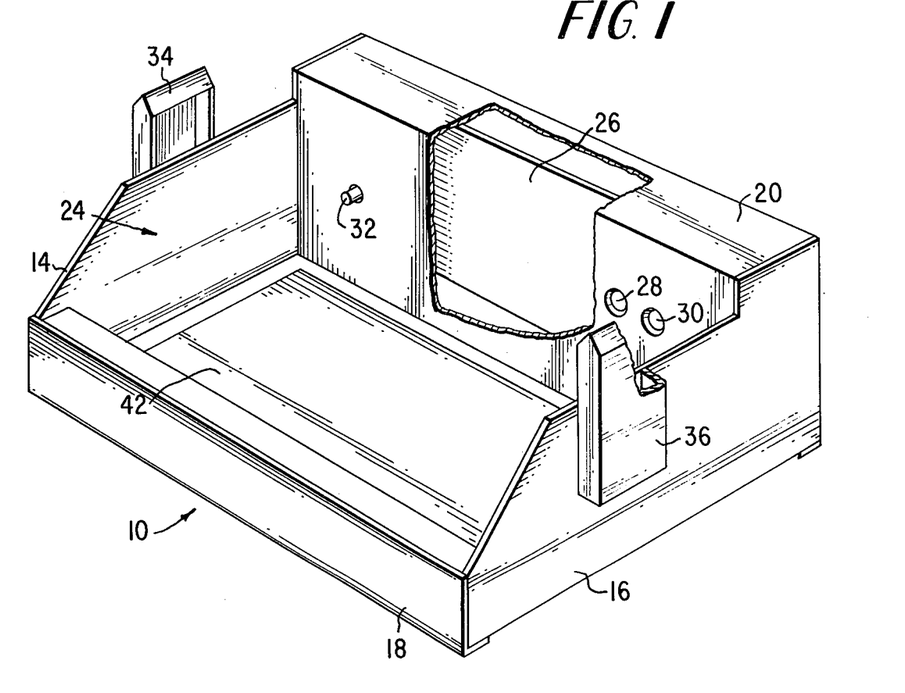
FIG. 1 is a perspective view of the outer support housing of the humidifier system of the present invention.
Figure 2:
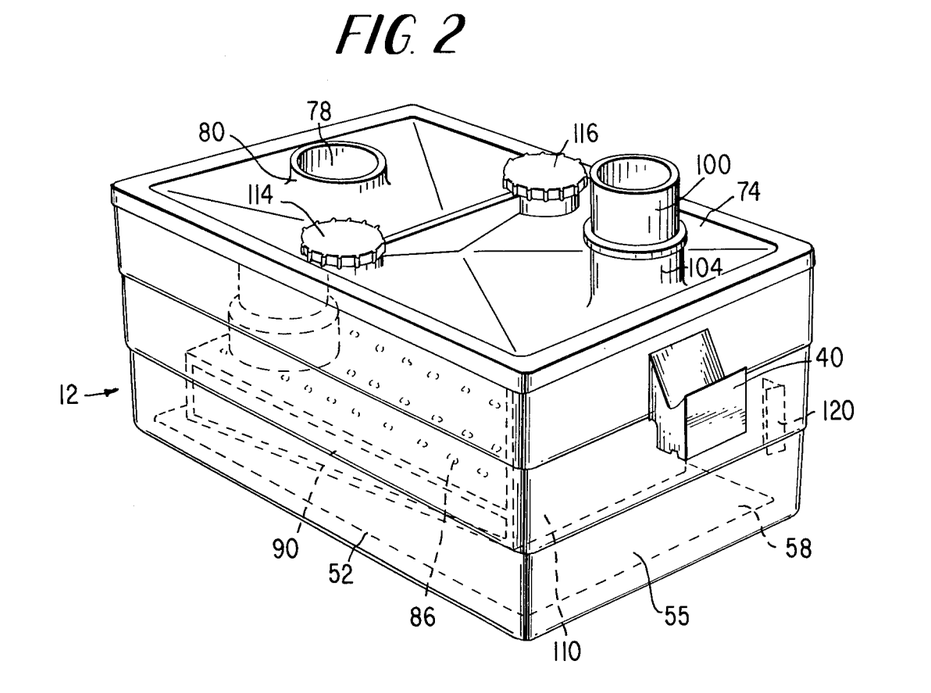
FIG. 2 is a perspective view of the water container for the humidifier system of the present invention; of FIG. 2 mounted in the housing of FIG. 1.

Turning now to a detailed consideration of the preferred embodiment of the invention illustrated in the drawings, with particular reference to FIGS. 1 and 2, there is illustrated at 10 a mounting base, or outer support housing, and at 12 an inner container or water tank adapted to be removably secured in the housing. These two elements, together with the controls and sensors associated with them, constitute the humidifier system of the present invention.

The outer housing 10 comprises a pair of side walls 14 and 16, a front wall 18, a hollow rear wall 20, and a bottom wall 22 which define a recess 24 adapted to receive the container 12. The housing, which may be of metal, plastic, or other suitable materials, is generally rectangular and is only slightly larger than the container, so that the container will be securely held and properly positioned within the housing so as to insure operation of the heating and sensing means located in the housing and to be described. The rear wall of the housing encloses a printed circuit board 26, or other circuit means for controlling the temperature of the water in container 12 and for sensing the level of the water. To accommodate the sensors, which in the present invention are solid state photoelectric devices secured to the circuit board, a pair of window openings 28 and 30 are provided in the rear wall. Also located in the rear wall is an actuator button 32 which serves as the operator for an interlock switch on the circuit board. The interlock switch functions to cut off power to the water heating element and to provide a "refill humidifier" indication when the container 12 is not in the housing.

Located on sidewalls 14 and 16 are a pair of clamps 34 and 36 of conventional design which serve to hold the water tank 12 in the housing. The clamps have an over-center snap action and are adapted to engage corresponding keepers 38 and 40 formed on the sides of container 12 (see FIGS. 2 and 3) and to pull the container downwardly toward the bottom of the housing. Located in the bottom of recess 24 formed by housing 10 is a heater element 42 which preferably consists of a conventional resistive heating pad 44 (FIG. 3) bonded to or otherwise mounted on a resilient base 46 of foam rubber or the like. The heating element 42 may be positioned in the recess by a peripheral frame member 48, if desired, or may be otherwise secured in the bottom of the housing to receive and engage the bottom of the container 12. When the container is secured in the housing, the clamps 34 and 36 press it downwardly against the resilient base 46 to insure that the container is held firmly in intimate engagement with the heater pad 44.

The heater pad is of conventional design, incorporating resistance heater wires arranged to produce a uniform thermal density of, for example, 5 watts/square inch and having an integral fail-safe overheat cut-off switch which serves to cut off electrical power to the heater element when its temperature exceeds a preset value such as 195° F. Embedded in the heater pad 44 is a thermistor bead 50, having a negative temperature coefficient of resistance, which is located adjacent the upper surface of the heater to contact the bottom of the container 12, thereby sensing the temperature of the bottom of the water tank. The thermistor is connected in the electrical control circuit to be described to provide a comparison voltage which is used to regulate the temperature of the heater pad 44.

Figure 3:
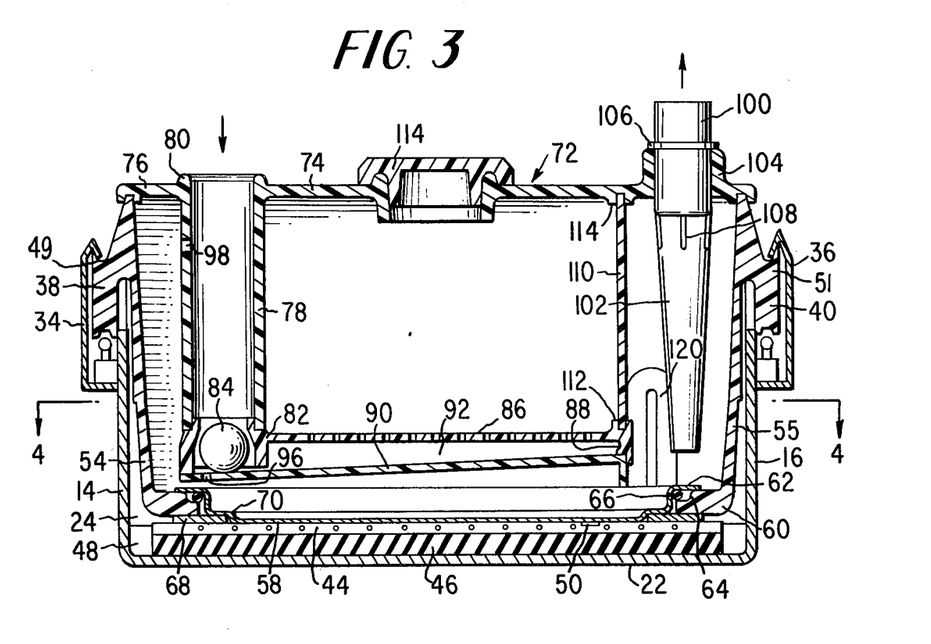
FIG. 3 is a cross-sectional view of the container of FIG. 2 mounted in the housing of FIG. 1.

As seen in FIG. 3, the clamps 34 and 36 engage upper shoulder portions 49 and 51 of the container keepers 38 and 40 to secure the container 12 in recess 24. These shoulder portions and the corresponding clamps are so shaped that when the clamps are snapped closed they become flush with the side walls 14 and 16, thereby forcing the container to be centrally located between the side walls. Further, the clamps and the corresponding container keepers serve to position the container between the front and rear walls so that it is properly located with respect to the heater pad 44, the windows 28 and 30, and the actuator button 32. Preferably, the clamps 34 and 36, and their corresponding container keepers, are off-center slightly to insure that the container can be secured in the housing only if it is correctly oriented.

Figure 4:
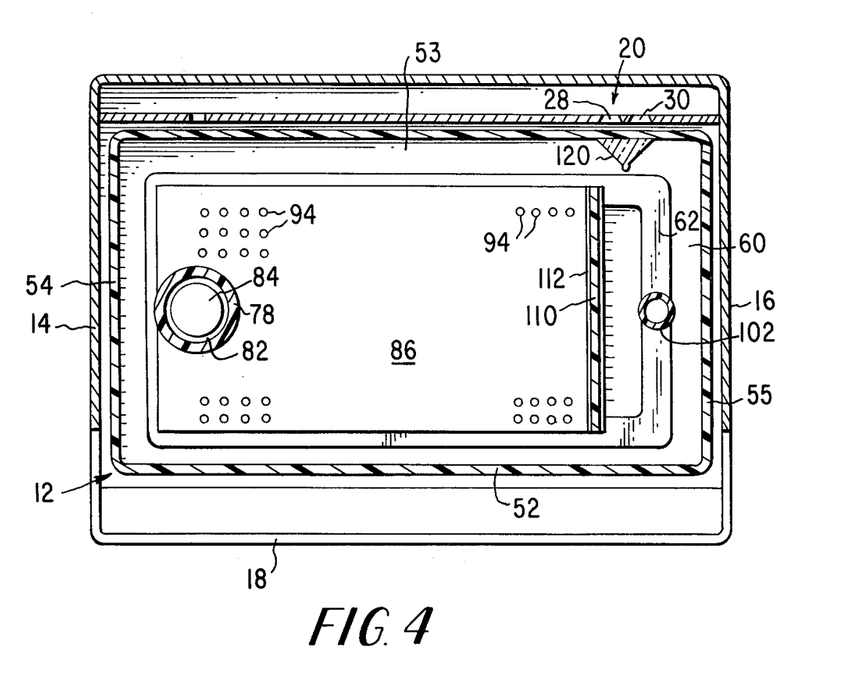
FIG. 4 is a cross-sectional view of the assembled humidifier, taken along line 4—4 of FIG. 3.

As shown in FIGS. 2, 3 and 4, the container 12 is formed by upstanding front, rear and side walls 52–55 of transparent plastic preferably molded in a single piece. The bottom of the container is closed by a thin metal plate 58 which may be of stainless steel or like material, and which is sealed to an inwardly extending bottom edge flange 60 formed by walls 52–55 to produce a water-tight container. As shown in FIG. 3, the bottom plate 58 incorporates a peripheral flange portion 62 which extends upwardly and outwardly to engage and rest on the inner surface of the wall flange 60. A peripheral shoulder 64 formed in the wall flange receives an O-ring 66 or other suitable gasket means to form a seal between the bottom plate 58 and the wall flange 60. The gasket 66 is held in sealing engagement between the plate and the wall flange by means of a stainless steel clamping ring 68 which is secured, as by spot welding, to the bottom surface of plate 58. As illustrated, the clamping ring fits in a peripheral depression 70 formed around the edge of plate 58 adjacent the flange portion 62 so that the ring can be secured substantially flush with the bottom surface of plate 58. The ring overlaps the outer, or bottom, surface of wall flange 60 so that the wall flange and the gasket 66 are gripped between flange 62 and clamping ring 68 upon assembly of the container. The thin metal bottom of the container is adapted to engage the upper surface of heater 42 and provides a good heat transfer medium between the heater and the water in container 12.

The top of the container is closed by a coverdiffuser assembly, generally indicated at 72, which in its preferred form is of plastic and is bonded or otherwise sealingly secured to the top of walls 52–55 to close the container 12. As illustrated in FIG. 3, the assembly includes a cover 74 formed with a peripheral groove 76 adapted to receive the upper edges of walls 52–55, and with an integral inlet tube 76. This tube has an upper shoulder portion 80 formed on the outer surface of the cover and is adapted to receive breathing gases from a respirator or other suitable source, as desired. The tube 78 extends downwardly to a point near the bottom of the container, where the terminal end of the tube is secured to a seat 82 of a ball-check valve having a positive buoyancy flow-check ball 84. The inlet of the valve receives the flow of gas from tube 78, with flotation ball tending to close the valve when the container is filled with water.

A diffuser plate 86 is secured at the lower end of tube 78, and in the preferred form is molded of plastic as a part of the valve seat 82 so as to extend horizontally across, but spaced from and generally parallel to, the bottom of the container. The diffuser plate is formed with a peripheral, downwardly extending skirt portion 88 to define a diffuser chamber. The skirt portion is adapted to receive a closure plate 90, the closure plate being secured to the bottom edge of the skirt portion to form a closed diffuser chamber 92 within the container 12. The closure plate 90 is secured between, and is spaced from, both the container bottom plate 58 and the diffuser plate 86, and is sloped away from the horizontal to form a tapered diffuser chamber. As seen in FIG. 3, the closure path is spaced below the valve ball 84, serving to contain the ball adjacent its valve seat 82 and insuring that the diffuser chamber 92 encompasses the outlet of the tube 78. Thus, air delivered to container 12 by way of tube 78 is directed through valve seat 82 into diffuser chamber 92.

As illustrated in FIG. 4, the diffuser plate 86 is provided with a large number, e.g., several hundred, small holes 94 which are spaced across the entire length and width of the plate. These holes extend between the diffuser chamber 92 and the interior of the container 12, whereby gas delivered to the chamber is diffused through holes 94 into the container. When the container is full of water, the diffused gas stream is broken into minute, macroscopic bubbles, thereby exposing a very large surface area of the gas to the water to accelerate the transfer of moisture to the gas.

In order to allow water to enter the closed diffuser chamber, bleeder holes 96 are provided in the diffuser closure plate 90. These holes allow water to seep into the diffuser chamber, while permitting the pressure of the entering gas to maintain a gas pocket just below the diffuser plate so that incoming gas is distributed across plate 86. A bleeder hole 98 is also provided near the upper end of tube 78 to permit pressure equalization.

As may be seen in FIGS. 2 and 4, the inlet tube 78 is located to one side of the container 12, with the diffuser chamber extending toward the other side thereof. Located at the other side of the container, beyond the end of the diffuser chamber, are an outlet tube 100 and a contamination trap 102 supported in a collar 104 formed on the cover 74. The outlet tube and the contamination trap may be separate elements or may be molded in one piece, and preferably are of plastic so that at least the trap portion 102 is conveniently disposable. The outer surface of the tube portion 100 is slightly tapered, as illustrated in FIG. 3, to mate with a corresponding tapered inner surface of collar 104, whereby the outlet and contamination trap may be removably secured in the container. The outlet tube portion 100 is provided with a shoulder 106 which serves to locate the trap within the container.

The upper end of the trap 102 is formed with a plurality of slot-like ports or openings 108 which lead to the interior of the outlet tube, and through which outlet gases flow. The top of the outlet tube 100 is shaped to receive conventional tubing through which breathing gas from the humidifier is carried to a patient. Trap 102 depends from the outlet and is closed at the bottom to receive any liquid backflow from the outlet tubing, thereby preventing such backflow from reaching the water supply in the humidifer. When the trap is full, it may be removed and discarded to reduce the threat of contamination of the humidifier supply and consequent injury to the patient.

When breathing gas bubbles upwardly through the water in the container, it is possible that small amounts of water can be thrown upwardly by the gas-created turbulence, and be carried into the outlet tube. To prevent this from occurring, a vertical baffle plate 110 is secured in the container between the end of the diffuser plate nearest the outlet and the cover 74. Baffle 110 may be bonded, or otherwise secured between a groove 112 formed on the upper surface of the diffuser plate 86 and a corresponding groove 114 formed on the inner surface of cover 74, and prevents a bubble turbulent water from entering the outlet ports 108.

A pair of access ports, closed by corresponding caps 114 and 116, are provided on co-diffuser assembly 72, as illustrated in FIGS. 2 and 3, to provide access to the interior of the humidifier for cleaning and/or sterilization and for the addition of water to the container. The caps fit tightly into the access ports to prevent leakage of breathing gases during operation of the humidifier.

Molded as a part of the container 12, preferably on the rear wall 53 thereof, is an optical prism 120 (FIG. 4) which cooperates with photoelectric devices located at windows 28 and 30 of the housing 10 to provide a remote detection of water level. The prism is so shaped and so located within the container that light beamed out of one of the windows 28 or 30 may be reflected by the angled surfaces of the prism back into the other one of windows 28 or 30. However, the outer surface of the prism 120 is not coated, so that a change in the refractive index of the medium surrounding the prism will change its reflectivity and thus change by a detectable amount the light returned to the other of the windows. Such a change in the medium surrounding the prism occurs when the level of water in the container changes, as illustrated in FIGS. 5–8, and thus the reflectivity of the prism provides a means for remotely sensing when the water level in the humidifier falls below a predetermined level.

Figure 5:
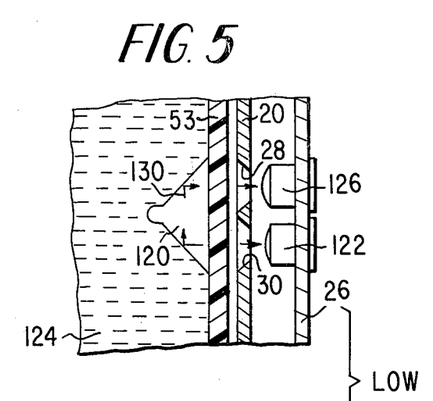
FIGS. 5–8 are top and side partial views of the optical level sensor of the present invention.
Figure 6:
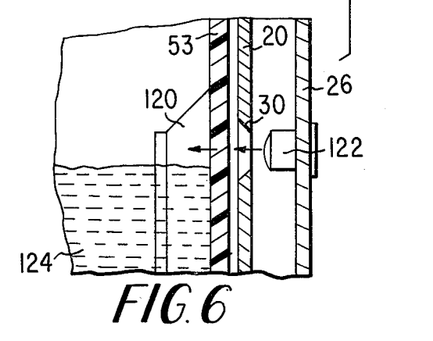
Figure 7:
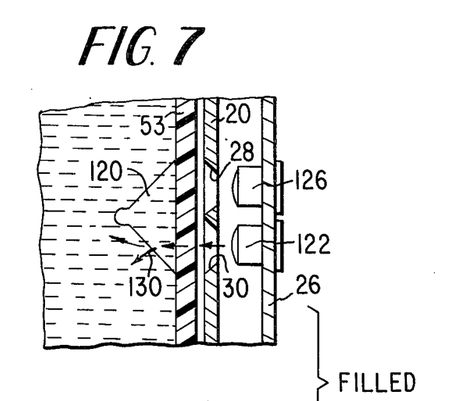
Figure 8:
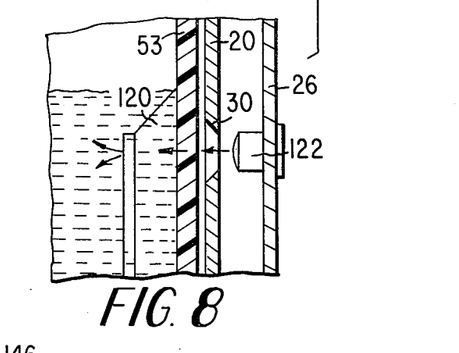

As shown in FIG. 5, the prism 120 is so located in the container 12 that the two right-angle surfaces of the triangular prism are aligned with windows 28 and 30 in the rear wall 20 of housing 10. Also aligned with window 30 and mounted on circuit board 26 is a light source such as a conventional light emitting diode (LED) 122 which produces infrared radiation. This radiation is directed to prism 120 where it is internally reflected if the level of the water 124 is below the point on the prism on which the radiation falls. Internally reflected light is directed by the prism to a photodetector 126, as shown in FIGS. 5 and 6, to activate the photodetector. If the water level is above the point on which the radiation falls, the interface between the water and the prism will be such that radiation will not be internally reflected, but will pass through the wall of the prism into the water, as indicated in FIGS. 7 and 8, providing substantially no signal at the photodetector. Thus the presence or absence of infrared radiation from the LED 122 at the photodetector 126 provides a signal representing inadequate or adequate water, respectively, in the humidifier, and this signal may be used to provide a suitable indication or alarm for the operator of the system.

It will be noted that the LED 122 is selected to have a very narrow dispersion of the beam of radiation, and the prism is large enough to insure that elements 122 and 126 can be spaced sufficiently far apart that light from the LED might be reflected from the exterior surface of the wall of container 12 will not reach the photodetector 126. Thus, the light reaching the photodetector must follow a path through the prism, thereby insuring an accurate reading. It has also been found that in the operation of a humidifier the heating and agitation of the water causes condensation and sprinkling of moisture on that part of the prism which would be above water level in a low water condition, and such condensation tends to provide a false indication of adequate water. However, false readings of this type may be avoided by increasing the gain of the photodetector amplifier so that any amount of light striking element 126 will be sufficient to indicate a low water level.

Figure 9:
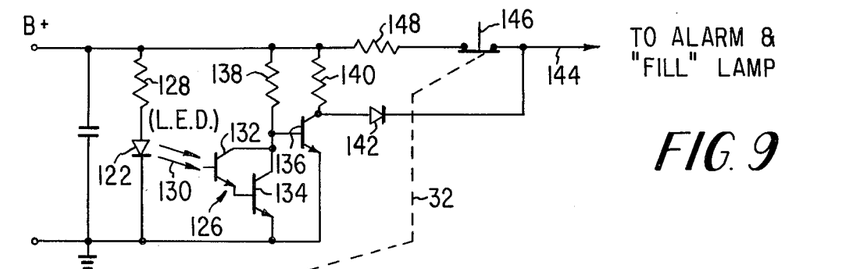
FIGS. 9 and 10 are schematic and partial block diagrams of the sensing and control circuits of the system of the present invention.

The photodetector devices 122 and 126 are connected in a sensing and indicating circuit such as that illustrated in FIG. 9, to which reference is now made. As illustrated, the LED device 122 is connected across a source of direct current through a resistor 128 and is energized thereby to produce infrared radiant energy, indicated by arrows 130. When such radiation falls on photodetector 126, which may comprise, for example, a photosensitive transistor 132 connected in a Darlington arrangement with a second transistor 134, an output signal appears on the base of a grounded emitter transistor 136. The collectors of the Darlington pair and of transistor 136 are connected to the direct current bias source through resistors 138 and 140, respectively, and the presence of a signal at the base of transistor 136 results in an output signal on the collector thereof which is fed through a blocking diode 142 to an output line 144. A signal on line 144 serves to activate a suitable alarm to provide warning that the water level in the container 12 is below the level of the light path through the prism 120. The alarm signal may also activate a lamp to provide a visual indication that the humidifier should be filled.

As illustrated in FIG. 9, the actuator button 32, described with respect to FIG. 1, serves to operate a normally closed interlock switch 146 which may be mounted on the circuit board 26 in alignment with the actuator. The normally closed contacts connect the bias supply source through a resistor 148 to the output line 144, whereby the alarm and fill lamps are normally activated. However, when the container 12 is placed in its housing 10, the container presses against actuator 32 and opens interlock switch 146, disabling the direct path between the bias source and output line 144. With this arrangement, then, removal of the container 12 provides a false "low water" indication and alarm which overrides the photodetector output, with diode 142 isolating transistor 136 from this false signal. Replacement of the container in the housing restores the alarm circuit to the control of the photodetector.

The temperature of the water within container 12 must be accurately controlled in order to regulate the amount of moisture in the breathing gas and in order to deliver to the patient gas of a desired temperature. To obtain this control, the circuit board 26 carries a control circuit such as that illustrated in FIG. 10, to which reference is now made. The basic control element for the present system is a zero voltage switch 150, which is a monolithic integrated circuit such as the CA3059 manufactured by RCA suitable for use as a trigger circuit for the control of thyristors in temperaturecontrol applications. As described in the Application Note LCAN-6158 on Linear Integrated Circuits, published by RCA Solid State Division, this circuit employs a diode limiter, a threshold detector, a differential amplifier, and a Darlington output driver to provide the basic switching action. The dc supply voltage for the circuit is supplied by an internal zener-diode-regulated power supply which may also be used to supply other external circuits. The trigger pulses developed by switch 150 appear on output line 152 and are applied directly to the gate of a triac 154 to provide current flow to the resistive heating element 156 of the heating pad 44. A failsafe circuit is built into switch 150 to inhibit the application of pulses to the triac gate in the event of a short or open circuit at the input to the switch.

Figure 10:
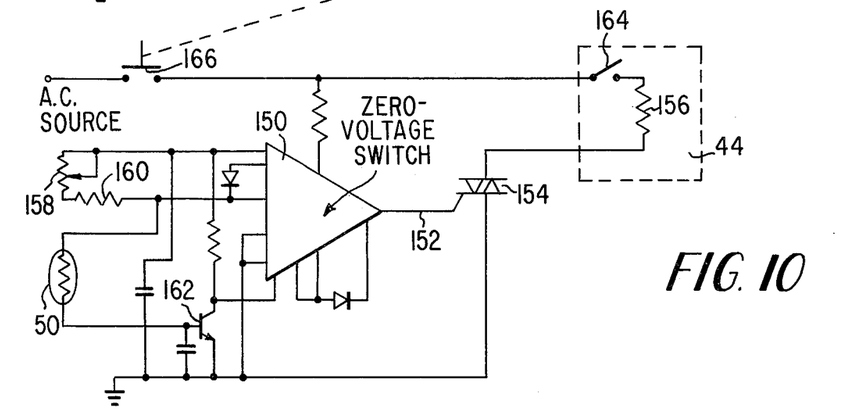

The operation of switch 150 is regulated by a control potentiometer 158, which preferably is located on a control panel (not shown) to permit adjustment of the water temperture, and the heating pad thermistor 50 which are connected in series through a resistor 60 to form a voltage dividing network. When the resistance of thermistor 50 is greater than that of potentiometer 158, the switch 150 will turn triac 154 on, completing a path from an alternating current source, through heating resistance 156. As the heating pad increases in temperature, the resistance of the thermistor decreases until the voltage drop across it becomes slightly less than the voltage across potentiometer 158 and resistor 160. The switch 150 will then cease to provide gating pulses to the triac, and the heating pad is deenergized.

Transistor 162 performs the fail-safe operation of this circuit, responding to open or short circuit conditions in the thermistor to shut off switch 150 and prevent further operation of the heating pad. An additional safety factor is provided by an integral overheat thermostat 164 built into the heating pad. This thermostat is normally closed, but responds to temperature within the pad in excess of 195° F to open the power circuit to the heating element 156, thereby insuring that the patient cannot be harmed by excessive water temperature. Since the normal control range of the system, as determined by potentiometer 158 and resistor 160, is between 70° and 180° F, the temperature at which thermostat 164 operates can only be reached by a system failure.

The power to heating element 156 is supplied through a normally open interlock switch 166 which is operated by means of the mechanical actuator 32 when the container 12 is positioned in the housing 10. Thus, alternating current cannot be supplied to the heating pad when the container has been removed from its housing; insertion of the container closes interlock 166 and allows the temperature control system to warm the water in the container to the selected temperature.

As will be apparent from the foregoing, the humidifier system of the present invention is operated by assembling the container unit, filling it with water, and inserting the outlet tube-contaminant trap in the outlet opening. The container water tank is filled to the desired level, below the level of the bleeder port 98 and outlet ports 108, by adding water through the access ports in the cover 72. The water enters the diffuser chamber 92 through bleeder 96 and traps an air pocket therein between the water surface and the bottom of the diffuser plate, the holes 94 being sufficiently small that the surface tension of the water will hold the air in place.

The container is placed in the recess 24 of housing 10 and secured by clamps 34 and 36, thereby pressing the bottom plate 58 against the surface of the heating pad, aligning the prism 120 with the LED 122 and the photodetector 126 to provide the optical level sensor, and actuating button 32 to operate the interlocking switches 146 and 166. The operation of the interlock switches places the system level alarm and indicator under the control of the optical sensor, and permits energization of the heating element by the heater control circuit to heat the water to the desired temperature. A breathing gas supply tube is connected to the inlet 78 to feed gas under positive pressure to the humidifier.

The water in the container 12 serves to float ball 84 against seat 82, closing this valve and preventing water from entering the inlet tube. When sufficient positive pressure is exerted by the inflowing breathing gas, the ball is displaced, and gas is supplied to the diffuser chamber 92, from which it is forced upwardly through the diffuser plate and through a substantial portion of the water in the container. The stream of inflowing gas is broken up into small bubbles which are warmed and humidified as they pass through the water. The warm, moisturized gas is then directed around baffle 110 to the outlet ports 108, and is carried to the patient through suitable breathing tubes.

Since the tubing leading to the patient often is cooler than the gas supplied by the humidifier, the gas is cooled and loses some of its moisture. Condensate forms on the wall of the tubing, and may flow back toward the humidifier. Since such backflowing condensate may occur in the tubing at or near the patient, it is often the case that it carries with it bacteria and other contaminants which may originate with the patient. If such bacteria is permitted to reach the water supply in container 12, it is apparent that the warm wet conditions therein may tend to encourage the growth of such organisms and result in injury to the patient. In the present invention, however, backflowing condensate passes into the contaminant trap 102, where it is held for disposal and is prevented from entering the water supply.

Although the present invention has been described in terms of a specific structure in order to facilitate the understanding of the concepts embodied therein, it will be understood by those of skill in the art that numerous modifications and variations may be made without departing from the true spirit and scope of the invention. For example, many of the elements described herein as being separate may, if convenient to the manufacture thereof, be formed in a single piece. Similarly, although plastic materials are contemplated for the water container, other materials may be utilized if desired. In a modified form of the invention, one of the access opening caps may be replaced by a fitting to permit sterile drip filling of the humidifier. These and other changes will be apparent and accordingly it is intended that the present application be limited only by the following claims.

What is claimed is:

1. A system for humidifying breathing gases, comprising:
    a support housing defining a recess;
    a heater means in said recess and carried by said support housing;
    container means for holding a supply of water, said container means including gas inlet and gas outlet means;
    means removably securing said container means in said recess in heat transfer relationship with said heater means;
    diffuser means within said container and spaced therefrom to define a diffuser chamber, said chamber being so located as to be below the surface of the supply of water during operation of said system and so located as to permit a free flow of water therearound, said diffuser means including a diffuser element for passing breathing gas upwardly out of said diffuser chamber;

means including said gas inlet means communicating with said diffuser chamber for directing said breathing gas into said diffuser chamber below the surface of the supply of water, said breathing gas thereafter passing upwardly through said diffuser element and the supply of water;

means including said gas outlet means communicating with the interior of said container to direct said breathing gas out of said container; and a contaminant trap connected to said gas outlet means and located within said container for receiving and retaining backflowing contaminated liquid which returns from said outlet means to said container.

2. The system of claim 1, further including optical sensing means responsive to the level of the supply of water in said container means, said sensing means having no moving parts and including a prism located within and forming an intergral part of the wall of said container means.

3. The system of claim 2, wherein said sensing means further includes photoelectric means carried by said support housing and located outside said container for directing light into said container and through said prism, the prism reflecting said light to said photoelectric means in accordance with the level of water in said container; and circuit means responsive to said photoelectric means to provide an indication of water level.

4. A system for humidifying a breathing gas, comprising:

container means adapted to receive a supply of water through which a breathing gas is passed for humidification, said container having bottom, wall and cover portions;

diffuser means mounted within said container and so located as to be below the surface of the water during operation of said system, said diffuser means including a diffuser plate defining the top wall of a diffuser chamber adjacent but smaller than the bottom portion of said container, said diffuser plate having a multiplicity of small apertures for passing breathing gas out of said chamber, and said diffuser chamber having side edges spaced from the wall portion of said container to permit free circulation of water around the diffuser chamber;

gas inlet means extending into said container and communicating with said diffuser chamber to direct breathing gas into said diffuser chamber, said breathing gas flowing from said diffuser chamber upwardly through said diffuser plate apertures whereby the gas is formed into streams of small bubbles for passage through the water in the container;

gas outlet means communicating with the interior of said container, said outlet means being located between a side edge of said diffuser and the wall portion of the container and above the surface of the water during operation of the system for collecting humidified breathing gas that has passed through the water; and baffle wall means located between said diffuser plate and said outlet means to prevent bubble turbulent water from entering said outlet means while permitting humidified gas to flow thereto.

5. The system of claim 4, further including optical sensing means responsive to the level of said supply of water, said sensing means including a prism formed as an integral part of said container means.

6. The system of claim 5, wherein said sensing means further includes photoelectric means located outside said container to direct light into said container and through said prism, the prism reflecting said light to said photoelectric means in accordance with the level of water in said container.

7. The system of claim 6, further including circuit means responsive to said photoelectric means to provide an indication of water level.

8. The system of claim 4, wherein said baffle wall means within said container is mounted on said diffuser plate to separate the area of bubble turbulent water above said diffuser plate from said outlet means, said baffle wall means being spaced from the wall portion of said container.

9. The system of claim 4, further including a contaminant trap located within said container and having an opening adjacent and below said outlet means to receive and retain backflowing liquid from said outlet means.

10. The system of claim 4, further including a diffuser closure plate secured to and spaced below said diffuser plate to define a closed diffuser chamber for receiving breathing gas from said gas inlet means.

11. The system of claim 10, further including a check valve connecting said inlet means to said diffuser chamber to prevent liquid from entering said inlet means from said container.

12. The system of claim 4, wherein said cover portion comprises a cover-diffuser assembly supporting said inlet means, outlet means, baffle means, and diffuser plate within said container and spaced from the wall and bottom portions thereof, said baffle means being secured between said cover portion and said diffuser plate.

13. The system of claim 4, further including housing means;

heater means carried by said housing;

means for removable securing said container in said housing in heat transfer relationship with said heater means;

level sensing means in said housing responsive to the level of water in said container and interlock means responsive to the presence of said container in said housing for activating said heater means and said level sensing means.

14. The system of claim 13, wherein said heater means comprises an electrical heating element mounted in said housing for heating said water in container, and temperature control means responsive to the temperature of the water.

15. The system of claim 14, wherein said temperature control means comprises a temperature sensor in heat exchange contact with the water, and control circuit means responsive to said sensor for maintaining the water, and thus sensor, at a predetermined temperature.

16. The system of claim 13, wherein said container means comprises a water tank having side walls, a bottom, and a cover, said container bottom having high heat conductivity and adapted to be in heat exchange relationship with said heater means when said container is secured in said housing.

* * * * *

UNITED STATES PATENT AND TRADEMARK OFFICE
CERTIFICATE OF CORRECTION

PATENT NO. : 4,028,444

DATED : June 7, 1977

INVENTOR(S) : Allen C. Brown, Neil R. Hattes, Theodore B. Eyrick

It is certified that error appears in the above—identified patent and that said Letters Patent are hereby corrected as shown below:

IN THE CLAIMS

Claim 13, line 4, "removable" should be --removably--.

Claim 14, line 3, "for heating said water in container" should read --for heating water in said container--.

Claim 15, line 5, "and thus sensor" should read --and thus said sensor--.

Signed and Sealed this twenty-third Day of August 1977

[SEAL]

Attest:

RUTH C. MASON
*Attesting Officer*

C. MARSHALL DANN
*Commissioner of Patents and Trademarks*